(12) United States Patent  
Isogai

(10) Patent No.: US 7,452,078 B2  
(45) Date of Patent: Nov. 18, 2008

(54) EYE REFRACTIVE POWER MEASUREMENT APPARATUS

(75) Inventor: Naoki Isogai, Nishio (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 11/527,571

(22) Filed: Sep. 27, 2006

(65) Prior Publication Data

US 2007/0070293 A1  Mar. 29, 2007

(30) Foreign Application Priority Data

Sep. 27, 2005  (JP)  ............................. 2005-280971

(51) Int. Cl.  
*A61B 3/10* (2006.01)

(52) U.S. Cl. ...................... 351/205; 351/221

(58) Field of Classification Search ......... 351/205–206, 351/212, 221  
See application file for complete search history.

(56) References Cited

U.S. PATENT DOCUMENTS

| | | | |
|---|---|---|---|
| 4,812,033 A | | 3/1989 | Ishikawa |
| 5,463,430 A | | 10/1995 | Isogai et al. |
| 5,751,396 A | * | 5/1998 | Masuda et al. ............ 351/221 |
| 5,905,562 A | * | 5/1999 | Isogai et al. ............. 351/208 |
| 6,033,074 A | | 3/2000 | Miyake et al. |
| 2004/0054277 A1 | * | 3/2004 | Uchida ..................... 600/399 |
| 2005/0068497 A1 | | 3/2005 | Hanebuchi et al. |
| 2005/0275804 A1 | * | 12/2005 | Masaki ..................... 351/208 |

FOREIGN PATENT DOCUMENTS

| | | |
|---|---|---|
| EP | 0 928 596 A1 | 7/1999 |
| EP | 1 402 810 A1 | 3/2004 |
| JP | A 1-129830 | 5/1989 |
| JP | A 6-46999 | 2/1994 |
| JP | A 2003-47593 | 2/2003 |
| JP | A 2005-103103 | 4/2005 |

* cited by examiner

*Primary Examiner*—Scott J. Sugarman  
*Assistant Examiner*—Dawayne A Pinkney  
(74) *Attorney, Agent, or Firm*—Oliff & Berridge, PLC

(57) ABSTRACT

An eye refractive power measurement apparatus by which an examiner can properly check reliability of a measurement result while time and effort of the examiner are saved. The eye refractive power measurement apparatus for measuring eye refractive power of an examinee's eye has a measurement optical system for projecting a measurement target onto a fundus of the eye to pick up a fundus reflection image by a two-dimensional image-pickup element, a storing device which stores the picked-up fundus reflection image as a measurement image, a display device, a measurement condition judging device which makes a judgment as to whether or not the stored measurement image satisfies a predetermined measurement condition, and a first display control device which controls the display device to display the stored measurement image when the measurement condition judging device judges that the measurement condition is not satisfied.

9 Claims, 6 Drawing Sheets

EYE REFRACTIVE POWER MEASUREMENT APPARATUS

BACKGROUND OF THE INVENTION

1. Field of the Invention

The present invention relates to an eye refractive measurement apparatus for measuring eye refractive power of an examinee's eye.

2. Description of Related Art

Conventionally, there is an eye refractive power measurement apparatus which projects a measurement target onto a fundus of an examinee's eye to pick up a fundus reflection image by a two-dimensional image-pickup element, stores the picked-up (detected) fundus reflection image as a measurement image, and obtains eye refractive power of the eye based on the stored measurement image. Proposed as this kind of apparatus is one which is capable of displaying the measurement image by operation of a display change over switch in order to check reliability of a measurement result (see Japanese Patent Application Unexamined Publication No. Hei1-129830).

However, it takes time and trouble to display the measurement image by operation of the display change over switch, and even if the measurement image is displayed, it is sometimes difficult for an unaccustomed examiner to check reliability of the measurement result.

SUMMARY OF THE INVENTION

An object of the invention is to overcome the problems described above and to provide an eye refractive power measurement apparatus by which an examiner can properly check reliability of a measurement result while time and effort of the examiner are saved.

To achieve the objects and in accordance with the purpose of the present invention, an eye refractive power measurement apparatus for measuring eye refractive power of an examinee's eye has a measurement optical system for projecting a measurement target onto a fundus of the eye to pick up a fundus reflection image by a two-dimensional image-pickup element, storing means which stores the picked-up fundus reflection image as a measurement image, display means, measurement condition judging means which makes a judgment as to whether or not the stored measurement image satisfies a predetermined measurement condition, and first display control means which controls the display means to display the stored measurement image when the measurement condition judging means judges that the measurement condition is not satisfied.

Additional objects and advantages of the invention are set forth in the description which follows, are obvious from the description, or may be learned by practicing the invention. The objects and advantages of the invention may be realized and attained by the eye refractive power measurement apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
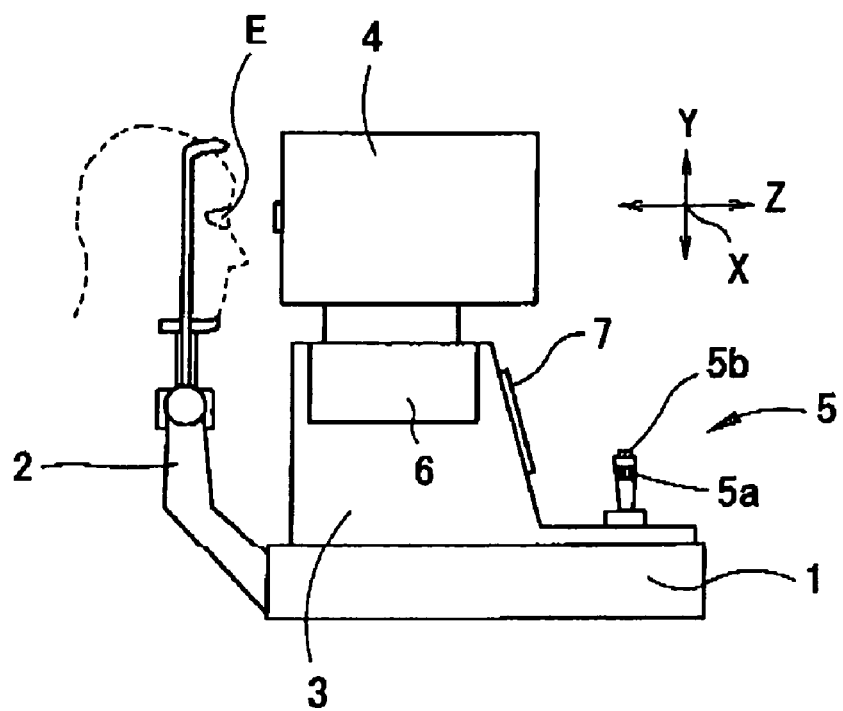
FIG. 1 is a schematic external view of an eye refractive power measurement apparatus consistent with one preferred embodiment of the present invention.

A detailed description of one preferred embodiment of an eye refractive power measurement apparatus embodied by the present invention is provided below with reference to the accompanying drawings. FIG. 1 is a schematic external view of the eye refractive power measurement apparatus consistent with one preferred embodiment of the present invention. The measurement apparatus includes a base 1, a face (head) supporting unit 2 attached to the base 1, a mobile base 3 provided movably on the base 1, and a measurement part (measurement unit) 4 provided movably on the mobile base 3 and housing a measurement optical system and the like. By tilting operation of a joystick 5, the mobile base 3 is moved in a right-and-left direction (hereinafter, an X-direction) and a back-and-forth direction (a working distance direction: hereinafter, a Z-direction). In addition, by rotating operation of a rotation knob 5a, the measurement part 4 is moved on the mobile base 3 in an up-and-down direction (hereinafter, a Y-direction). In addition, the measurement part 4 is moved in the X,Y,Z-directions with respect to an eye E of an examinee by an XYZ movement part 6 provided to the mobile base 3. At the tip of the joystick 5, a measurement starting switch 5b is provided. In addition, a monitor 7 is provided on the mobile base 3.

Figure 2:
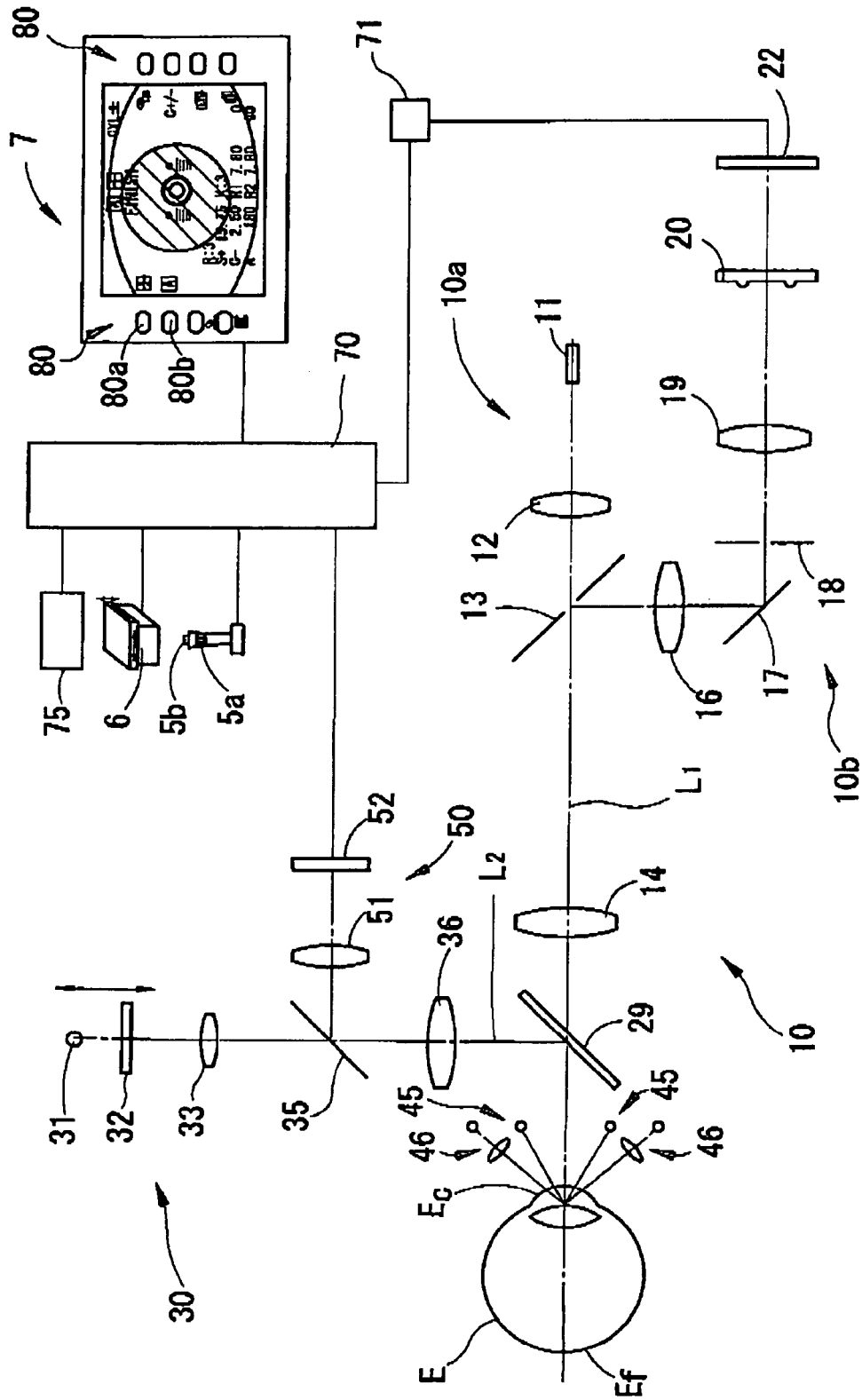
FIG. 2 is a view showing a schematic configuration of an optical system and a control system of the present apparatus.

FIG. 2 is a view showing a schematic configuration of an optical system and a control system of the measurement apparatus. A measurement optical system 10 includes a projection optical system 10a for projecting a measurement target (measurement light) in a spot shape onto a fundus Ef via a central pupillary portion of the eye E, and a photo-receiving optical system 10b for picking up fundus reflection light in a ring shape via a peripheral pupillary portion of the eye E and picking up a fundus reflection image in a ring shape by a two-dimensional image-pickup element.

The projection optical system 10a includes an infrared light source 11 for measurement, a relay lens 12, a hole mirror 13 and an objective lens 14 for measurement, which are placed on an optical axis L1 of the measurement optical system 10. The light source 11 is placed in a position optically conjugate with the fundus Ef of the eye E with emmetropia. In addition, an opening of the hole mirror 13 is placed in a position optically conjugate with a pupil of the eye E.

Figures 3A, 3B:
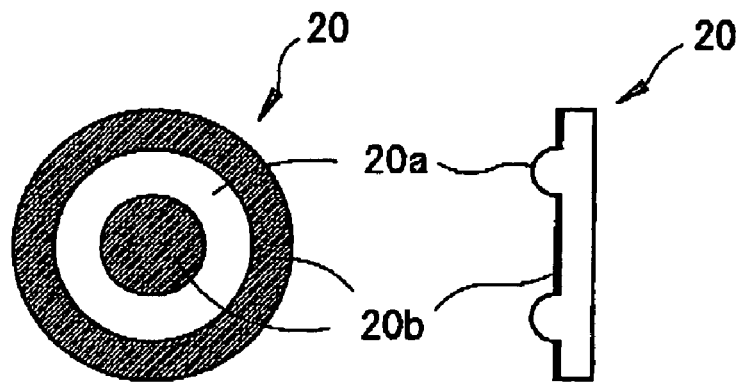
FIGS. 3A and 3B are views showing a schematic configuration of a ring lens.

The photo-receiving optical system 10b shares the objective lens 14 and the hole mirror 13 with the projection optical system 10a, and includes a relay lens 16 and a total reflection mirror 17 which are placed on the optical axis L1 in a reflecting direction of the hole mirror 13, and a photo-receiving diaphragm 18, a collimator lens 19, a ring lens 20 and a two-dimensional image-pickup element 22 such as an area CCD which are placed on the optical axis L1 in a reflecting direction of the total reflection mirror 17. The photo-receiving diaphragm 18 and the image-pickup element 22 are placed in positions optically conjugate with the fundus Ef. As shown in FIGS. 3A and 3B, the ring lens 20 is constituted of a lens portion 20a which is a cylindrical lens formed in a ring shape on one side of a transparent plate, and a light shielding portion 20b formed of coating for light shielding which is provided to the portions other than the ring-shaped cylindrical lens forming the lens portion 20a, and is placed in a position optically conjugate with the pupil. Output from the image-pickup element 22 is inputted to a calculation and control part 70 via an image memory 71.

Incidentally, the measurement optical system is not limited to the one mentioned above, and known ones may be employed, for example, one which projects a measurement target (measurement light) in a ring shape onto the fundus via the peripheral pupillary portion, picks up fundus reflection light via the central pupillary portion, and picks up a fundus reflection image in a ring shape by a two-dimensional image-pickup element.

A fixation target presenting optical system 30 includes a visible light source 31 for fixation-target presentation, a fixation target plate 32, a projection lens 33, a dichroic mirror 35 transmitting visible light and reflecting infrared light, and an objective lens 36 for observation, which are placed on an optical axis L2 made coaxial with the optical axis L1 by a half mirror 29. The light source 31 and the fixation target plate 32 are movable in the direction of the optical axis L2 in order to perform fogging on the eye E.

In front of the half mirror 29, ring target projection optical systems 45 for projecting an infrared ring target onto a cornea Ec of the eye E, and infinite target projection optical systems 46 for projecting infrared infinite targets for detecting an alignment state in the Z-direction with respect to the eye E are placed symmetrically about the optical axis L1. Incidentally, the ring target projection optical systems 45 double as an anterior segment illumination optical system for illuminating an anterior segment of the eye E, and may also be used as a target projection optical system for corneal shape measurement.

An observation optical system 50 shares the objective lens 36 and the dichroic mirror 35 with the fixation target projection optical system 30, and includes an image-pickup lens 51 and a two-dimensional image-pickup element 52 which are placed on the optical axis L2 in a reflecting direction of the dichroic mirror 35. Output from the image-pickup element 52 is inputted to the calculation and control part 70. Accordingly, an image of the anterior segment of the eye E is picked up by the image-pickup element 52 to be displayed on the monitor 7. Incidentally, the observation optical system 50 doubles as a target image detection optical system for detecting an image of the ring target and images of the infinite targets.

The calculation and control part 70 is connected with the image-pickup element 52, the image memory 71, a memory 75, the knob 5a, the switch 5b, the XYZ movement part 6, the monitor 7, a switch part 80 having a plurality of switches and used for various settings, and the like. Placed on the switch part 80 are an alignment mode change over switch 80a for making a change over between an automatic alignment mode and a manual alignment mode, a measurement mode change over switch 80b for making a change over between an automatic measurement mode in which a trigger signal for starting measurement is automatically generated upon completion of alignment and a manual measurement mode in which a trigger signal for starting measurement is generated by operation of the switch 5b, and the like. The calculation and control part 70 controls the entire apparatus, and performs calculation of eye refractive power, calculation of a corneal shape and the like.

Figure 4:
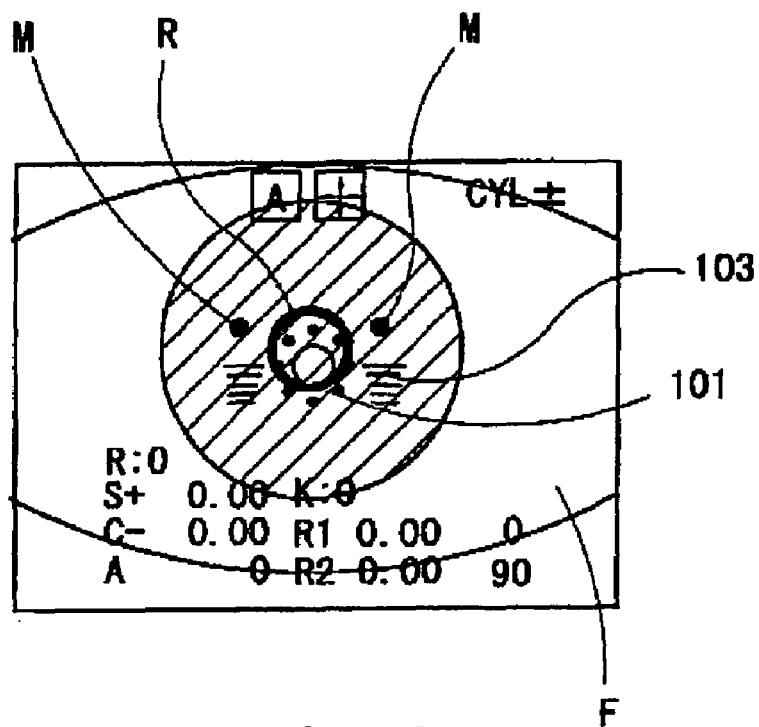
FIG. 4 is a view showing a display example of an alignment screen including an anterior segment image for observation.

Measurement operations of the apparatus with the above-mentioned configuration will be described. First, the alignment of the measurement part 4 (measurement optical system 10) with respect to the eye E is performed by making a face (head) of the examinee fixed to the face supporting unit 2 and making the eye E fixate a fixation target. Thereby, the anterior segment image of the eye E is picked up by the image-pickup element 52, and on the monitor 7, an anterior segment image F for observation, a ring target image R by the ring target projection optical systems 45, and infinite target images M by the infinite target projection optical systems 46 are displayed (see FIG. 4).

In the case of the automatic alignment mode, the calculation and control part 70 detects an alignment state of the measurement part 4 with respect to the eye E based on the output from the image-pickup element 52. In this case, based on the central position of the detected ring target image, the calculation and control part 70 obtains the alignment state in the X,Y-directions of the measurement part 4 with respect to the eye. In addition, based on a distance between the detected infinite target images and a space in a predetermined meridional direction of the ring target image, the calculation and control part 70 calculates the alignment state in the Z-direction of the measurement part 4 with respect to the eye E (for details, see U.S. Pat. No. 5,463,430 corresponding to Japanese Patent Application Unexamined Publication No. Hei6-46999). Then, the calculation and control part 70 drives and controls the XYZ movement part 6 based on detection results on the alignment states to automatically perform alignment of the measurement part 4 with respect to the eye E.

In addition, in the case of the manual alignment mode, the examiner operates the joystick 5 while observing the ring target image R displayed on the monitor 7, and adjusts a position of the measurement part 4 in the X,Y-directions so that the ring target image R and a reticle mark 101 become concentric circles. In addition, the examiner adjusts a position of the measurement part 4 in the Z-direction with reference to an indicator 103 (or so that the ring target image R becomes thinnest).

In the case of the automatic measurement mode, measurement is automatically started upon completion of the alignment. On the other hand, in the case of the manual measurement mode, measurement is started when the alignment is completed and the examiner operates the switch 5b.

The calculation and control part 70 controls to light the light source 11 based on input of the trigger signal for starting measurement. The measurement light emitted from the light source 11 is projected onto the fundus Ef via the relay lens 12 to the half mirror 29 and forms a point light source image in a spot shape on the fundus Ef.

The light of the point light source image formed on the fundus Ef is reflected and scattered to exit the eye E, is converged by the objective lens 14, passes through the hole mirror 13 to the total reflection mirror 17 to be converged again on an opening of the photo-receiving diaphragm 18, is made to be approximate parallel light by the collimator lens 19 (if the eye E is emmetropia), is picked up as ring-shaped light by the ring lens 20, and is picked up by (photo-received on) the image-pickup element 22 as a ring image.

In measurement of the eye refractive power, preliminary measurement is firstly performed, and based on a result of the preliminary measurement, the light source 31 and the fixation target plate 32 are moved in the direction of the optical axis L2 to perform fogging on the eye E. Next, main measurement is performed on the eye E under fogging.

Figure 5:
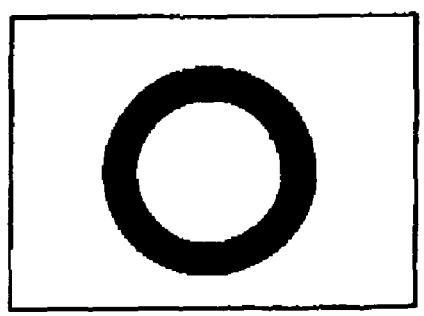
FIG. 5 is a view showing a measurement image (ring image)

FIG. 5 is a view showing the ring image picked up by the image-pickup element 22 during measurement. The output from the image-pickup element 22 is stored in the image memory 71 as image data (a measurement image). Thereafter, based on the measurement image stored in the image memory 71, the calculation and control part 70 obtains positions in meridian directions of the ring image. In this case, the calculation and control part 70 obtains positions of the ring image by calculating the middle and a peak of a waveform, a barycenter and the like of a brightness signal. Next, based on the obtained positions of the ring image, the calculation and control part 70 performs least square fitting of ellipses to obtain an ellipse. Then, the calculation and control part 70 obtains refractive errors in the meridian directions based on the shape of the obtained ellipse, obtains eye refractive power (sphere power, cylinder power and an astigmatic axial angle) of the eye E based on the refractive errors, and controls the monitor 7 to display the eye refractive power as a measurement result.

In the measurement, in order to enhance reliability of the measurement result, the calculation and control part 70 judges the measurement result as measurement error when a predetermined measurement condition is not satisfied, and controls the monitor 7 to display a judgment result. Here, the display control of the monitor 7 based on the measurement error will be described referring to the flowchart in the case of the automatic measurement mode (see FIG. 6).

Figure 6:
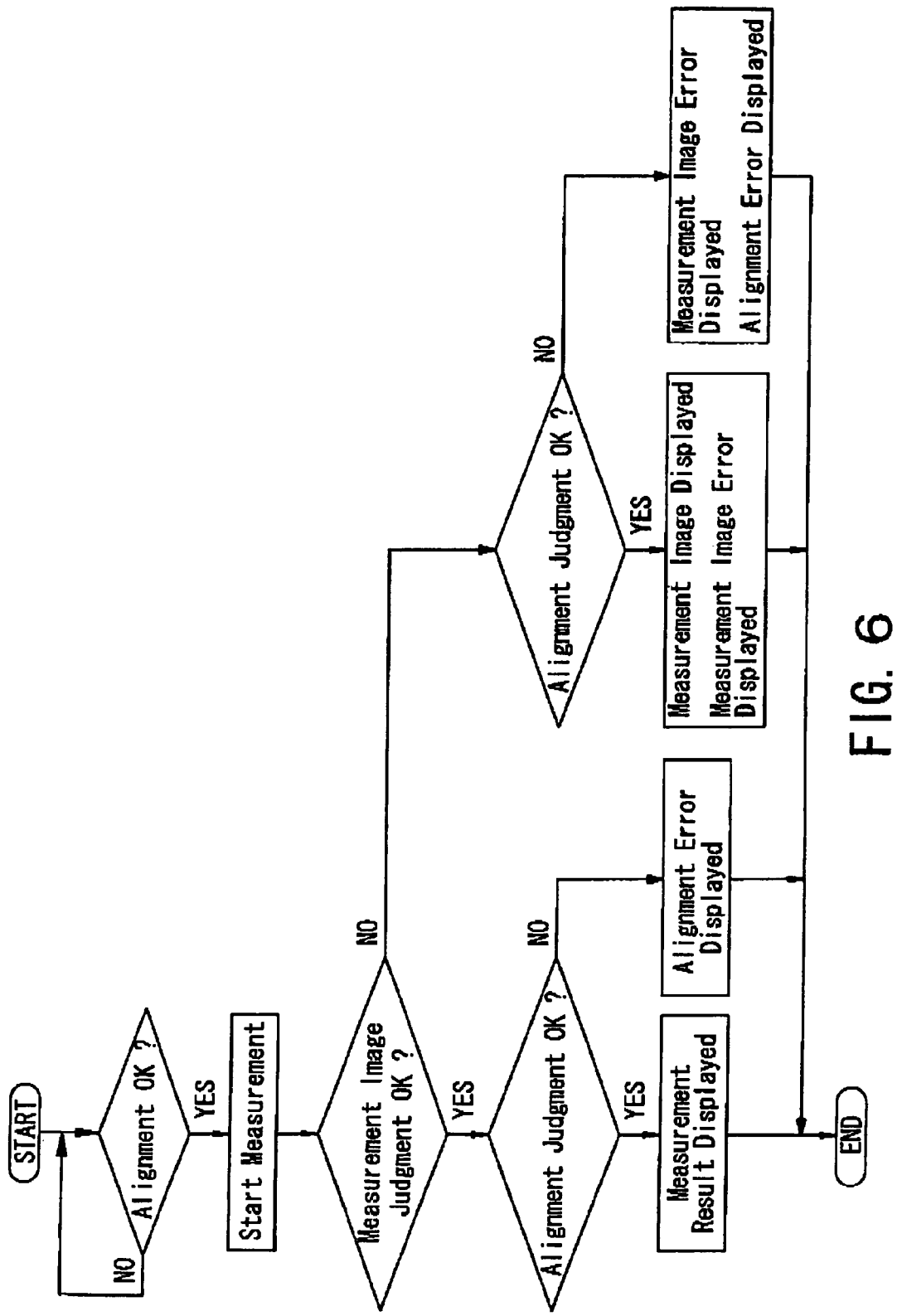
FIG. 6 is a flowchart for illustrating display control of a monitor based on measurement error in an automatic measurement mode.

The calculation and control part 70 automatically starts measurement when judges that the alignment state is appropriate. As shown in FIG. 6, the calculation and control part 70 makes a judgment as to whether or not the measurement image stored in the image memory 71 satisfies the predetermined measurement condition and a judgment as to whether or not the alignment state of the measurement part 4 (measurement optical system 10) with respect to the eye E during measurement is appropriate.

Figure 7:
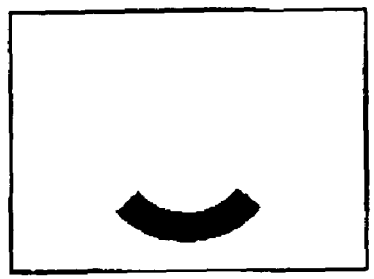
FIGS. 7A to 7D are views showing examples of a measurement image (ring image) for which it is considered proper to be judged as measurement image error (measurement error)
Figure 7:
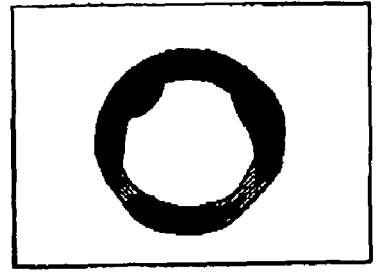
Figure 7:
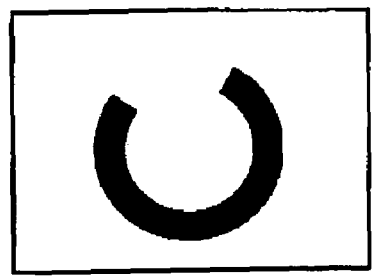
Figure 7:
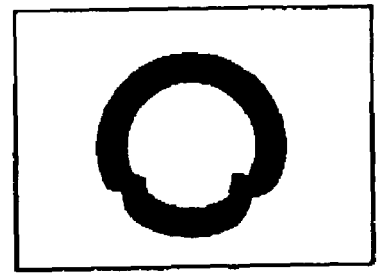

First, described is the judgment as to whether or not the measurement image satisfies the predetermined measurement condition. FIG. 7A to 7D are views showing examples of the measurement image for which it is considered proper to be judged as measurement image error in this judgment. FIG. 7A is a view showing a state of the ring image of which an upper side is missing because of a blink of the eye E during measurement. FIG. 7B is a view showing a state of the ring image in which an abnormal reflection image unintentionally appears in the peripheral part because of scatter of light caused by opacity of an optic media portion (a crystalline lens and the like) of the eye E. FIG. 7C is a view showing a state of the ring image of which an upper side is missing because the eye E has a small pupil. FIG. 7D is a view showing a state of the ring image in which irregular distortion is unintentionally generated because the eye E has irregular astigmatism. In any of these cases, detection of the position of the ring image and the like cannot be performed with high accuracy. Incidentally, the ring image shown in FIG. 5 is an example of a normal measurement image.

As for a method to make a judgment as to whether or not the measurement condition is satisfied, the degree of a missing part of the ring image (for example, whether or not more than half of the ring image is missing) is judged by detecting whether or not peak values of the brightness signals in the meridian directions of the ring image exceed a predetermined threshold value. In addition, the degree of the abnormal reflection image in the peripheral part of the ring image is judged by detecting whether or not the peak values of the brightness signals of the ring image, the width in a predetermined meridian direction of the ring image and the like exceed predetermined threshold values. In addition, the degree of a difference between the shape of the ellipse obtained when the ring image is subjected to ellipse fitting and the shape of the actual ring image is judged. Incidentally, the measurement condition may be a combination of a plurality of measurement conditions.

Next, the judgment as to whether or not the alignment state is appropriate is described. The judgment as to whether or not the alignment state during measurement is appropriate is made because there are not a few cases where the alignment is deviated by movement of the eye E during measurement (during obtainment of the measurement image) If the alignment deviation occurs during measurement, reliability of the measurement result is lowered.

In order to judge an alignment deviation exceeding a predetermined amount which could lower reliability of the measurement result, as alignment error, the calculation and control part 70 makes a judgment as to whether or not the alignment deviation of the measurement part 4 with respect to the eye E during measurement is within a predetermined allowable range (for example, whether or not a deviation from each alignment reference position in the X,Y,Z-directions is within 0.5 mm). Incidentally, the judgment as to whether or not the alignment state during measurement is appropriate includes not only judgment performed based on the ring target image and the infinite target images detected during measurement but also judgment performed based on the ring target images and the infinite target images detected before and after measurement. If the alignment states before and after measurement are appropriate, it is possible to consider the alignment state during measurement to be appropriate.

After the measurement image is stored in the image memory 71, and if the measurement image is judged to satisfy the measurement condition and the alignment state is judged to be appropriate, the calculation and control part 70 controls the monitor 7 to display the measurement result.

After the measurement image is stored in the image memory 71, and if the measurement image is judged to satisfy the measurement condition and the alignment state is judged to be not appropriate, the calculation and control part 70 does not control to display the measurement image and controls the monitor 7 to display a message saying alignment error (or, simply, measurement error). Incidentally, the alignment screen during measurement (for example, the anterior segment image) previously stored may be displayed on the monitor 7.

Figure 8:
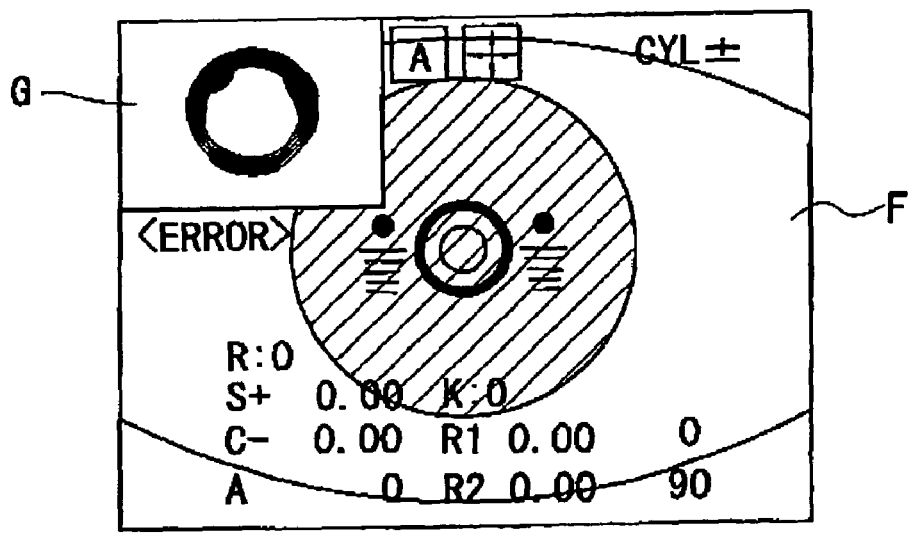
FIG. 8 is a view showing a display example of the measurement image.

After the measurement image is stored in the image memory 71, and if the measurement image is judged not to satisfy the measurement condition and the alignment state is judged to be appropriate, the calculation and control part 70 controls the monitor 7 to display a measurement image G stored in the image memory 71. For example, the measurement image G is displayed in a part of a monitor screen while superimposed on the anterior segment image F (see FIG. 8).

In this case, the monitor 7 is preferably controlled to display a massage saying measurement image error (or, simply, measurement error).

After the measurement image is stored in the image memory 71, and if the measurement image is judged not to satisfy the measurement condition and the alignment state is judged to be not appropriate, the calculation and control part 70 does not control to display the measurement image and controls the monitor 7 to display a message saying measurement image error and alignment error (or, simply, measurement error).

By displaying the measurement image on the monitor 7 when it is judged to be the measurement image error and the alignment state is judged to be appropriate after measurement as mentioned above, the examiner can properly specify the cause of the measurement image error based on the measurement image. Incidentally, if the measurement image is displayed when it is also judged to be the alignment error, the cause of the measurement image error is difficult to specify because disturbance occurs in the measurement image by the influence of the alignment deviation. Therefore, the measurement image is not displayed in such a case. Thereby, the examiner can obtain information as to whether or not the examinee's eye is an eye with cataract, irregular astigmatism, or the like, which is useful information in subsequent subjective examination and the like. In addition, by specifying the cause of the measurement image error, the examiner can take proper measures in response to the respective causes.

Incidentally, it is preferable to perform the display control as mentioned above only in the case of the automatic measurement mode. This is because, in the case of the manual measurement mode, there are such cases that measurement is performed intentionally with the alignment state being not appropriate when an eye with a pupil with eccentricity is measured, and that measurement is performed on an eye of an examinee which cannot be measured because of alignment failure in the automatic measurement mode. In such circumstances, the calculation and control part 70 controls to display the measurement image irrespective of the alignment state with respect to the eye E if it is judged to be the measurement image error.

Incidentally, when the monitor 7 is controlled to display the measurement image, a message specifically saying the cause of the measurement image error may be displayed. To be more specific, the calculation and control part 70 automatically specifies the cause of the measurement image error based on the measurement image stored in the image memory 71, and controls to display a message saying the specified cause of the measurement image error (such as letters and graphics) along with the measurement image. For example, two ring images pickup up at different times are previously stored in the memory 71 to be compared, and in a case where one of them does not have a missing part and the other one has a missing part, or the like, a message saying the occurrence of blink (for example, "BLINK") is displayed. In a case where the peak values of the brightness signals of the ring image, the width in the predetermined meridian direction of the ring image and the like exceed the predetermined threshold values, a case where the ring image has a plurality of missing parts, or the like, a message saying the presence of opacity (for example, "CATARACT") is displayed. In a case where the ring image has a missing part even though the alignment state is appropriate, or the like, a message saying an eye with a small pupil (for example, "SMALL PUPIL") is displayed. In a case where the difference between the shape of the ellipse obtained when the ring image is subjected to ellipse fitting and the shape of the actual ring image is great, or the like, a message saying an eye with irregular astigmatism (for example, "IRREGULAR") is displayed. In a case where the measurement image has characteristics unique to an eye in which an intraocular lens is implanted, a message saying an eye in which an intraocular lens is implanted (for example, "IOL") is displayed. Incidentally, if there are a plurality of causes of the measurement image error, a plurality of messages may be displayed, or a message saying a more likely cause of the measurement image error or a message saying a cause with greater influence on the measurement image error may be displayed. By such operation, the examiner can check the cause of the measurement image error visually.

Figure 9:
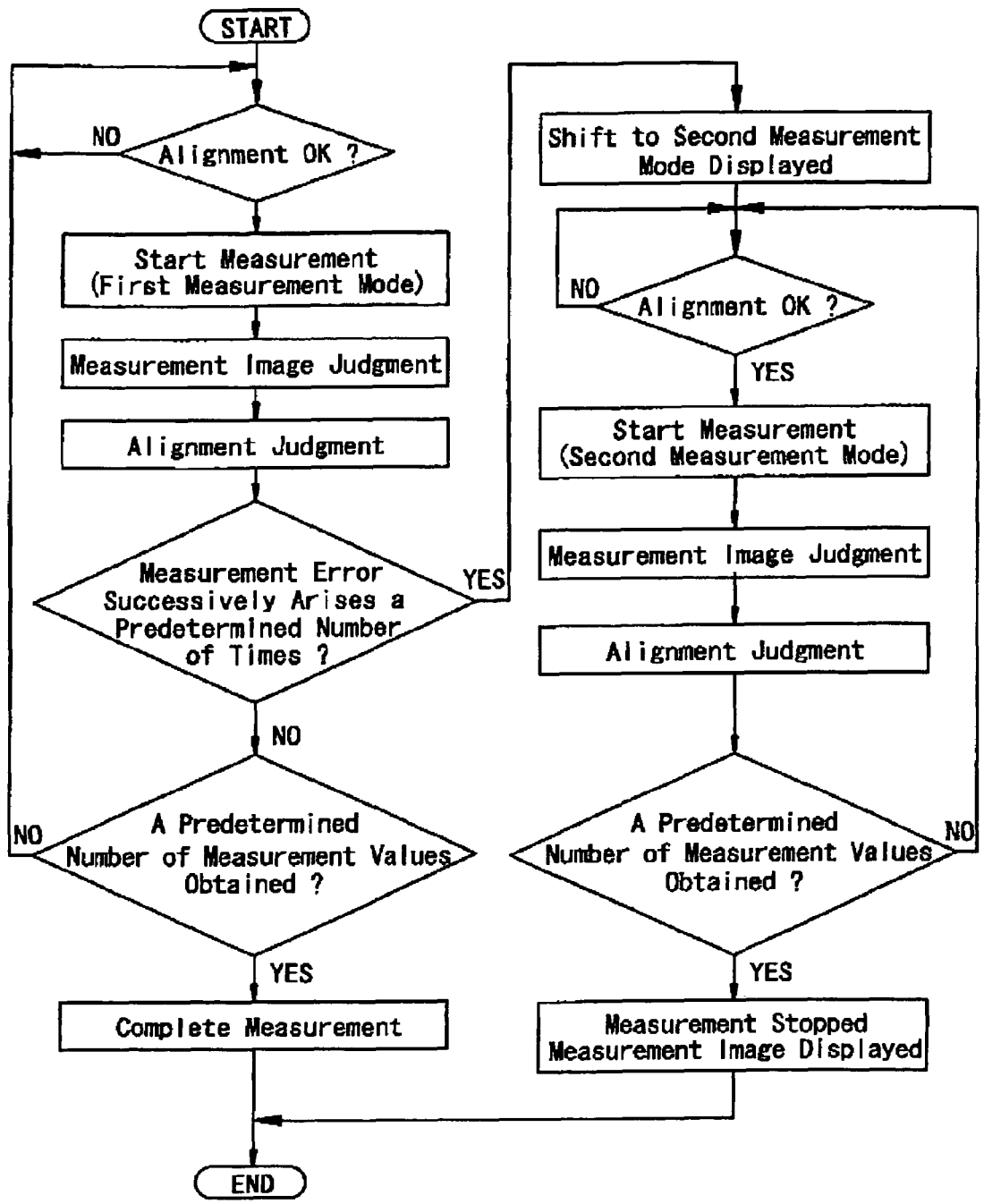
FIG. 9 is a flowchart for illustrating display control of the monitor based on measurement error in a case where there are an ordinarily-used first measurement mode for making a judgment as to whether or not the measurement image satisfies a predetermined first measurement condition, and a second measurement mode for makes a judgment as to whether or not the measurement image satisfies a predetermined second measurement condition which is more relieved than the first measurement condition.

Next, described will be the display control of the monitor 7 based on the measurement error when there are an ordinarily used first measurement mode for making a judgment as to whether or not the measurement image satisfies a predetermined first measurement condition and a second measurement mode for making a judgment as to whether or not the measurement image satisfies a predetermined second measurement mode which is more relieved than the first measurement condition, referring to the flowchart in the case of the automatic measurement mode (see FIG. 9). As for the second measurement mode, for example, when utilizing the degree of the missing part of the ring image as the measurement condition, whether or not more than three quarters of the ring image is missing is regarded as the second measurement condition, while whether or not more than half of the ring image is missing is regarded as the first measurement condition in the first measurement mode. Incidentally, in the second measurement mode, the eye E which causes the measurement error in the first measurement mode is intended to measure; accordingly, the light quantity of the light source 11 may be increased, or gain of the image-pickup element 22 may be increased.

The calculation and control part 70 firstly performs the eye refractive power measurement in the first measurement mode and, if the measurement error successively arises a predetermined number of times (for example, three times) before obtaining a predetermined number of (for example, three) measurement values without the measurement error, automatically shifts to the second measurement mode.

When shifted to the second measurement mode, the measurement condition is relieved; therefore, even if the eye E has opacity, irregular astigmatism, or the like, there increases a possibility that the predetermined number of measurement values are obtained while not considered as the measurement error. Hence, upon obtaining the predetermined number of measurement values without the measurement error in the second measurement mode, the calculation and control part 70 controls the monitor 7 to display the measurement image stored in the image memory 71 along with the measurement result. In this case, the measurement image obtained in the second measurement mode is preferably displayed.

As mentioned above, when the measurement result is obtained only in the second measurement mode, by displaying the measurement image, the examiner can specify the cause of the shift from the first measurement mode to the second measurement mode (the cause of the measurement error in the first measurement mode) based on the measurement image.

Incidentally, after the completion of the measurement on both the eyes, and when a change over of the eye to be measured is made by moving the measurement part 4, a change over between the measurement image of the right eye and the measurement image of the left eye may be made to display on the monitor 7. In other words, based on a signal from a measured eye detection part (a signal of the change over of the eye to be measured), the change over of the measurement image to display is made. In addition, the measurement image of the right eye and the measurement image of the left eye may be displayed together on the monitor 7.

In addition, it is also available to provide a first display mode for displaying the measurement image on the monitor 7 when judged as the measurement error as mentioned above, and a second display mode for displaying the measurement image on the monitor 7 irrespective of the judgment result on the measurement error, so that a display mode of the measurement image can be selected based on a selection signal from a mode selecting switch for selecting which mode to use, which is in the switch part 80. Owing to such configuration, selecting the second display mode allows the examiner to check the measurement image when the measurement error does not arise; accordingly, the examiner can check that there are no causes that may produce measurement error, based on the measurement image. In addition, the measurement image when the measurement error arises and the measurement image when the measurement error does not arise can be visually compared. In this case, if the examiner becomes accustomed to specifying the cause of the measurement error from the measurement image in the second display mode, it also becomes possible to employ the first display mode.

Incidentally, in the above description, the measurement image is displayed when judged as the measurement error; however, it is also available that a reliability coefficient indicating the degree of reliability of the measurement result in stages is calculated, and the display of the measurement image is controlled based on a result of the calculation. As a method to calculate the reliability coefficient, considered is a method of obtaining amounts of deviation between the shape of the ellipse obtained when the measurement image stored in the image memory 71 is subjected to ellipse fitting and the ring shape of the actual measurement image in the meridian directions, and calculating the reliability coefficient based on the degree of the sum total of the deviation amounts. More specifically, the degree of reliability is expressed as the reliability coefficient in six stages of 9, 8, 7, 6, 5, E (E is a minimum value of the reliability coefficient).

When utilizing the reliability coefficient as above, the measurement value is displayed while assigned the reliability coefficient, and the measurement image is displayed on the monitor 7 when the calculated reliability coefficient is below a predetermined value (for example, the reliability coefficient of 7). By such operation, the measurement image is displayed when the reliability coefficient utilized in checking reliability of the measurement result is low, so that the examiner can specify the cause of lowering the reliability coefficient based on the measurement image. Then, the examiner can take proper remedies in response to the specified cause.

In addition, the size of the measurement image displayed on the monitor 7 may be changed in response to the degree of the measurement error, the degree of the reliability coefficient, and the like. For example, when the reliability coefficient is utilized as mentioned above, the measurement image is displayed to be small if the reliability coefficient is 7, and the measurement image is displayed to be large if the reliability coefficient is E. By such operation, the degree of the reliability coefficient can be recognized from the size of the measurement image.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An eye refractive power measurement apparatus for measuring eye refractive power of an examinee's eye, the apparatus comprising:
   a measurement optical system for projecting a measurement target onto a fundus of the eye to pick up a fundus reflection image of the measurement target as a ring image by a two-dimensional image-pickup element;
   storing means which stores the picked-up ring image as a measurement image;
   display means;
   measurement condition judging means having a first measurement condition and a second measurement condition which is more relieved than the first measurement condition for making a judgment as to whether or not the measurement image is appropriate, which makes a judgment as to whether or not the stored measurement image satisfies the first measurement condition or the second measurement condition to be applied;
   an alignment state detection means which detects an alignment state of the measurement optical system with respect to the eye;
   an alignment state judging means which makes a judgment as to whether or not the alignment state of the measurement optical system with respect to the eye during measurement is appropriate, based on a detection result of the alignment state detection means; and
   a first display control means which controls the display means to display an alignment error message when the alignment state judging means judges that the alignment state during measurement is not appropriate, controls the display means to display the stored measurement image with an error message when the alignment state judging means judges that the alignment state during measurement is appropriate and the measurement condition judging means judges that the stored measurement image does not satisfy the first measurement condition in a case where the first measurement condition is applied, and controls the display means to display the stored measurement image with a measurement value when the alignment state judging means judges that the alignment state during measurement is appropriate and the measurement condition judging means judges that the stored measurement image satisfies the second measurement condition in a case where the second measurement condition is applied.

2. The eye refractive power measurement apparatus according to claim 1, further comprising:
   second display control means which controls the display means to display the stored measurement image irrespective of a judgment result of the measurement condition judging means; and
   selecting means which selects to use either one of the first display control means and the second display control means.

3. An eye refractive power measurement apparatus, the apparatus comprising:
   a measurement optical system for projecting a measurement target onto a fundus of the eye to pick up a fundus reflection image of the measurement target as a ring image by a two-dimensional image-pickup element;

storing means which stores the picked-up ring image as a measurement image;

display means;

measurement condition judging means which makes a judgment as to whether or not the stored measurement image satisfies a predetermined measurement condition;

an alignment state detection means which detects an alignment state of the measurement optical system with respect to the eye;

an alignment state judging means which makes a judgment as to whether or not the alignment state of the measurement optical system with respect to the eye during measurement is appropriate, based on a detection result of the alignment state detection means;

a first display control means which controls the display means to display the stored measurement image when the alignment state judging means judges that the alignment state during measurement is appropriate and the measurement condition judging means judges that the stored measurement image does not satisfy the measurement condition; and a cause specifying means which specifies, when the measurement condition judging means judges that the stored measurement image does not satisfy the measurement condition, a cause thereof, wherein the first display control means controls the display means to display the specified cause.

4. An eye refractive power measurement apparatus for measuring eye refractive power of an examinee's eye, the apparatus comprising:

a measurement optical system for projecting a measurement target onto a fundus of the eye to pick up a fundus reflection image of the measurement target as a ring image by a two-dimensional image-pickup element;

a storing means which stores the picked-up ring image as a measurement image;

a calculation means which obtains a measurement value of the eye refractive power based on the stored measurement image, the calculation means obtaining a reliability coefficient indicating the degree of reliability of the measurement value in stages based on the stored measurement image;

a display means which displays the obtained measurement value;

a measurement condition judging means which makes a judgment as to whether or not the stored measurement image satisfies a predetermined measurement condition; and a display control means which controls the display means to display the stored measurement image irrespective of a judgment result made by the measurement condition judging means, and the display controls means controls the display means to display the measurement value while assigned the obtained reliability coefficient.

5. The eye refractive power measurement apparatus according to claim 4, further comprising:

a mode selecting means for selecting either one of a mode for controlling the display means to display the stored measurement image irrespective of the judgment result made by the measurement condition judging means, and a mode for controlling the display means to display the stored measurement image when the measurement condition judging means judges that the stored measurement image does not satisfy the measurement condition.

6. The eye refractive power measurement apparatus according to claim 4, further comprising:

an alignment state detection means which detects an alignment state of the measurement optical system with respect to the eye; and an alignment state judging means which makes a judgment as to whether or not the alignment state of the measurement optical system with respect to the eye during measurement is appropriate, based on a detection result of the alignment state detection means, wherein the display control means controls the display means to display a message indicating an alignment error when the alignment state judging means judges that the alignment state during measurement is not appropriate.

7. The eye refractive power measurement apparatus according to claim 4, wherein the display control means controls the display means to display the measurement value when the measurement condition judging means judges that the stored measurement image satisfies the measurement condition, and controls the display means to display a message indicating a measurement image error when the measurement condition judging means judges that the stored measurement image does not satisfy the measurement condition.

8. The eye refractive power measurement apparatus according to claim 4, further comprising:

a cause specifying means which specifies, when the measurement condition judging means judges that the stored measurement image does not satisfy the measurement condition, a cause thereof, wherein the display control means controls the display means to display the specified cause.

9. The eye refractive power measurement apparatus according to claim 4, further comprising a control means which increases one of a light quantity of a light source included in the measurement optical system and a gain of the image-pickup element when the measurement condition judging means judges that the stored measurement image does not satisfy the measurement condition.

* * * * *